(12) United States Patent
Koehl et al.

(10) Patent No.: US 6,356,349 B1
(45) Date of Patent: Mar. 12, 2002

(54) POLARITON WAVE IMAGING

(75) Inventors: Richard A. Koehl, Huntsville, TX (US); Satoru Adachi, Hyogo (JP); Keith A. Nelson, Newton, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/350,972

(22) Filed: Jul. 9, 1999

Related U.S. Application Data

(60) Provisional application No. 60/092,429, filed on Jul. 10, 1998.

(51) Int. Cl.[7] .............................................. G01N 21/01
(52) U.S. Cl. ..................................................... 356/432
(58) Field of Search ............................ 356/432, 432 T; 359/239, 237

(56) References Cited

U.S. PATENT DOCUMENTS

| | | | |
|---|---|---|---|
| 5,116,121 A | | 5/1992 | Knoll et al. |
| 5,182,666 A | * | 1/1993 | Kawabe ..................... 359/107 |
| 5,275,168 A | | 1/1994 | Reintjes et al. |
| 5,418,797 A | | 5/1995 | Bashkansky et al. |
| 5,451,785 A | | 9/1995 | Faris |
| 5,623,145 A | | 4/1997 | Nuss |
| 5,710,430 A | | 1/1998 | Nuss |
| 5,999,308 A | * | 12/1999 | Nelson et al. ............... 359/237 |
| 6,075,640 A | * | 1/2000 | Nelson ....................... 359/239 |

OTHER PUBLICATIONS

Auston et al., "Electrooptic Generation and Detection of Femtosecond Electrical Transients," *IEEE Journal of Quantum Electronics*, 24:184–197, Feb. 1988.

Vallee et al., "Picosecond Phonon–Polariton Pulse Transmission Through an Interface," *Physical Review Letters*, 74:3281–3284, Apr. 17, 1995.

Vallee et al., "Temporal and Spatial Evolution fo Picosecond Phonon–Polariton Pulses in Crystals," *Physical Review B*, 46:799–812, Dec. 1, 1992.

* cited by examiner

Primary Examiner—F L. Evans
Assistant Examiner—Zandra V. Smith
(74) Attorney, Agent, or Firm—Fish & Richardson P.C.

(57) ABSTRACT

A method for characterizing a polariton wave within a material includes: generating the polariton wave; and imaging the polariton wave with optical radiation to produce a spatially-resolved image of portions of the optical radiation affected by the polariton wave. The method can be used to identify inhomogeneities in the material, detect electrical signals within the material, or characterize a polariton wave propagating within a waveguide, e.g., a waveguide formed within a photonic crystal. The optical imaging can be based on diffraction, polarization rotation, or spectral filtering of optical probe radiation transmitted through, or reflected by, the material.

23 Claims, 9 Drawing Sheets

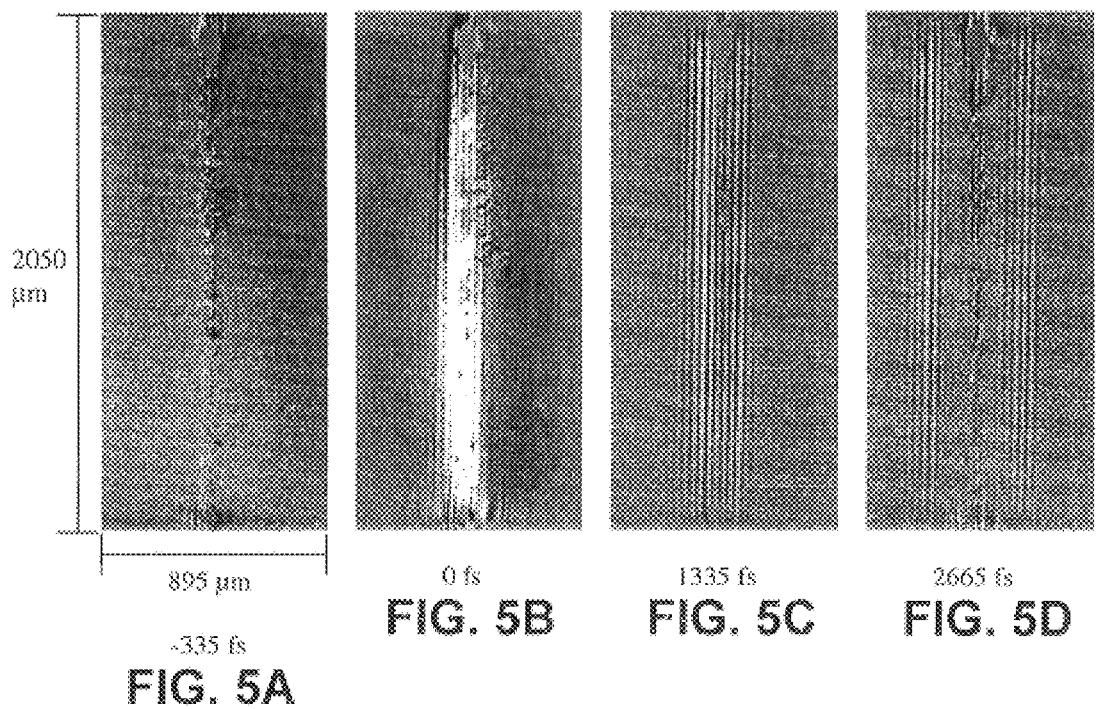
2050 μm
895 μm
-335 fs
FIG. 5A
0 fs
FIG. 5B
1335 fs
FIG. 5C
2665 fs
FIG. 5D
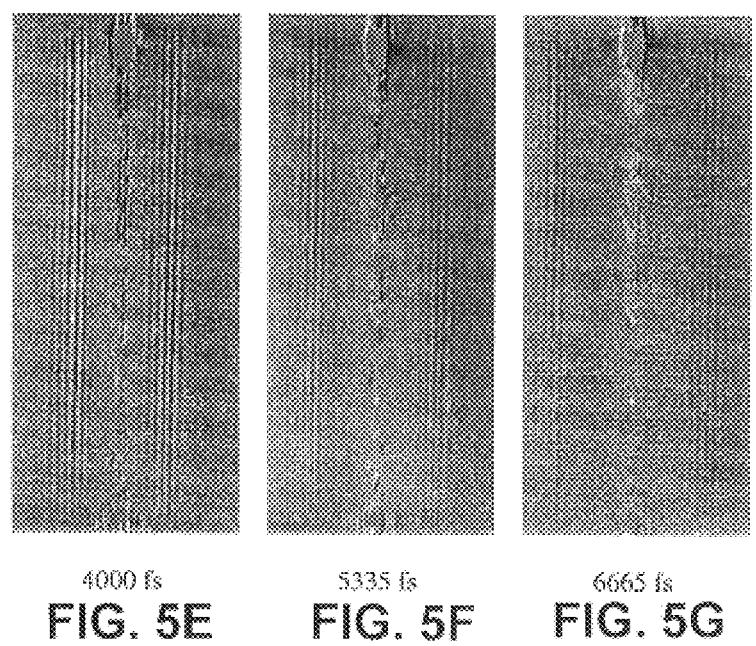
4000 fs
FIG. 5E
5335 fs
FIG. 5F
6665 fs
FIG. 5G

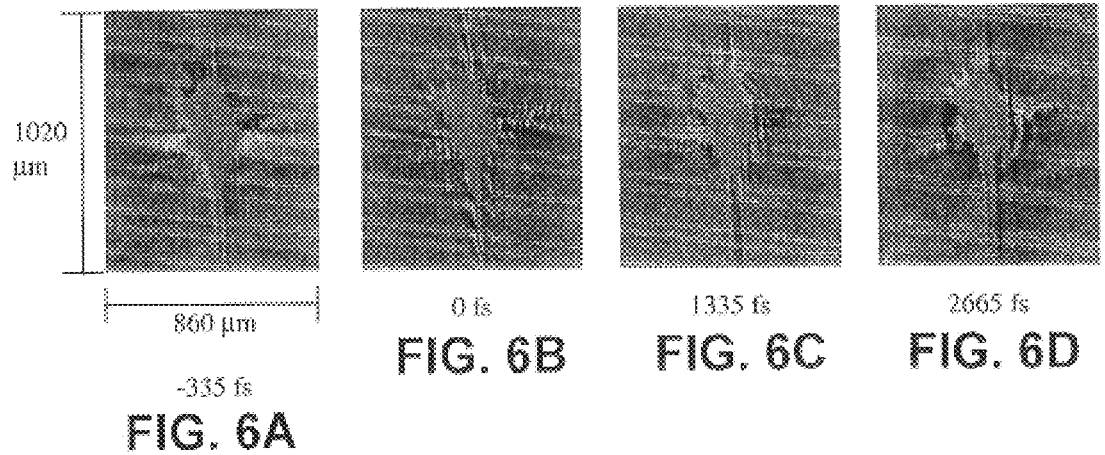
-335 fs
FIG. 6A
0 fs
FIG. 6B
1335 fs
FIG. 6C
2665 fs
FIG. 6D
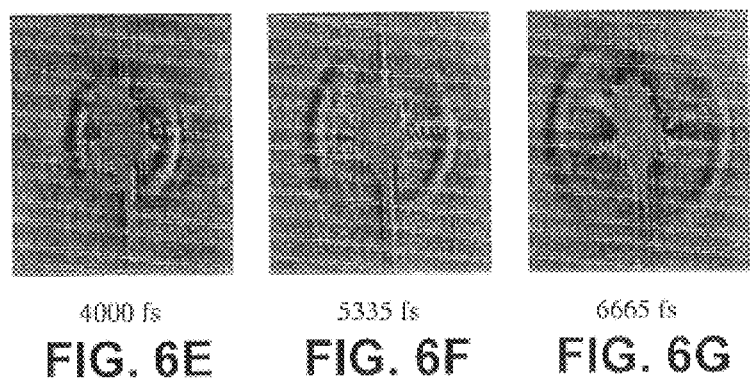
4000 fs
FIG. 6E
5335 fs
FIG. 6F
6665 fs
FIG. 6G

POLARITON WAVE IMAGING

CROSS-REFERENCE TO RELATED APPLICATIONS

This application claims the benefit of U.S. Provisional Application No. 60/092,429, filed Jul. 10, 1998, the contents of which are incorporated herein by reference.

STATEMENT AS TO FEDERALLY SPONSORED RESEARCH

This invention was made with Government support under CHE-9713388 awarded by the National Science Foundation. The Government has certain rights in this invention.

BACKGROUND OF THE INVENTION

This invention relates to methods for optically characterizing materials and signals carried therein.

Semiconductor and ferroelectric structures, such as DRAMS and CMOS circuits, are common in microelectronic, optoelectric, and photonic devices. Such structures often include multiple materials and layers, which may be separately processed, e.g., by chemical vapor deposition, ion-doping, and annealing, and patterned, e.g., by microlithography and ion-etching. Once fabricated, such structures often carry signals during use, e.g., charge carriers. Characterizing such structures and signal paths therein is important for developing new devices and manufacturing methods, and for assessing the quality of fabrication lines mass-producing existing devices.

Material structures can be characterized by local physical properties, such as stiffness, complex refractive index, and density. Waves propagating in the material structure can be indicative of such properties. For example, acoustic waves propagating within the material structures can be indicative of local stiffness variations.

SUMMARY OF THE INVENTION

The invention feature methods for characterizing a material, or signals therein, by imaging polariton waves propagating within the material. The methods and systems involve generating a polariton wave in the sample, allowing the polariton wave to propagate, and optically generating an image of the polariton wave. The image characterizes the propagation of the polariton wave, e.g., its spatially resolved direction, amplitude, and phase, at a time during or subsequent to the generation of the polariton. Imaging the polariton wave at multiple time intervals during and after its generation provides a series of images characterizing the time-dependent spatial propagation of the polariton wave. Since the phase velocity, attenuation, and direction of the polariton waves are sensitive to physical properties of the material, such as complex refractive index or dielectric constant, the polariton images are indicative of local and time-dependent variations in such properties. For example, the images can be indicative of material inhomogeneities including crystalline defects, domain wall boundaries, patterned structures, and other features fabricated deliberately or otherwise present that may scatter the polariton waves. Also, the images may indicate the presence of transient or dc electrical signals in the material since such signals may affect polariton propagation. Furthermore, in some embodiments, the material may be a device that uses polariton waves as signal carriers. In such embodiments the images characterize the polariton signal path, which may be important in diagnosing the efficacy of the device.

In general, in one aspect, the invention features a method for characterizing a polariton wave within a material. The method includes generating a polariton wave in the material and imaging the polariton wave with optical radiation to produce a spatially-resolved image of portions of the optical radiation affected by the polariton wave. The optical radiation may have a central wavelength in the range of about 300 nm to 2.5 microns.

In general, in another aspect, the invention features a method for characterizing polariton propagation within a material. The method includes: generating a polariton wave at a first spatial location in the material; waiting for a time interval sufficient to allow the polariton wave to propagate to additional spatial locations in the material; and optically imaging the polariton wave at the additional spatial locations. The polariton wave may have an electromagnetic frequency within the range of, e.g., about 300 GHz to 20 THz.

The optically imaging may include directing optical radiation to the additional spatial locations and generating a spatially-resolved image of portions of the optical radiation affected by the polariton. Also, the method may further include repeating the waiting and imaging steps for additional time intervals; and generating a spatially-resolved image of the polariton wave for each of the time intervals based on each of the imaging steps. Furthermore, the method may include identifying inhomogeneities in the material based on the images or detecting electrical signals within the material based on the images.

The polariton wave may be generated a number of ways. For example, it may be generated by converting fast electrical signals adjacent the first spatial location into the polariton or it may be generated optically, e.g., by crossing a pair of optical excitation beams on the material to form an optical excitation grating pattern at the first spatial location. Optical pulses having a durations shorter than 1 ps may be used to optically generate the polariton wave.

The optical imaging may be performed a number of ways. For example, it may be based on diffraction, polarization rotation, or spectral filtering of optical probe radiation that is transmitted through, or reflected from, the material. The material may be, e.g., a semiconductor or a ferroelectric.

Furthermore, the optical radiation directed to the additional spatial locations may have a size greater than or equal to about 1 mm. Also, the optical radiation directed to the additional spatial locations may have a size that overlaps the first spatial location.

In general, in a further aspect, the invention features a method for characterizing a polariton wave propagating within a waveguide. The method includes: introducing the polariton wave into a first location of the waveguide; waiting for a time interval sufficient to allow the polariton wave to propagate to additional locations within the waveguide; and optically imaging the polariton wave at the additional spatial locations.

The waveguide may formed in a photonic crystal. Also, the method may further include repeating the waiting and imaging steps for additional time intervals and generating a spatially-resolved image of the polariton wave for each of the time intervals based on each of the imaging steps.

The methods described above may have a number of advantages. For example, materials can be characterized based on polariton images. Furthermore, since each image provides information about multiple spatial regions of the material, the method provides a rapidly-acquired and intuitive "picture" of the material response to polariton generation. Also, the methods and systems described above may be used as diagnostics for devices having complex material structures or structures used to carry signals.

Other features, aspects, and advantages will be apparent from the following detailed description, and from the claims.

BRIEF DESCRIPTION OF THE DRAWING

FIGS. 5a–5g are images of polariton propagation collected using the apparatus of FIG. 4.

FIGS. 6a–6g are images of polariton propagation collected using an apparatus similar to that of FIG. 4, except that only a single, circularly focused pump beam was used.

DETAILED DESCRIPTION

The invention features methods for spatial imaging of propagating electromagnetic and vibrational waves, i.e., polariton waves, in bulk and thin film materials including semiconductor and ferroelectric devices. The polariton images may be used to detect position-dependent variations in material properties, including defects, thin film delamination, domain boundaries, and patterning in fabricated devices. The polariton images may also be used to detect transient or dc electrical signals that affect polariton propagation.

General System and Method

Figure 1A:
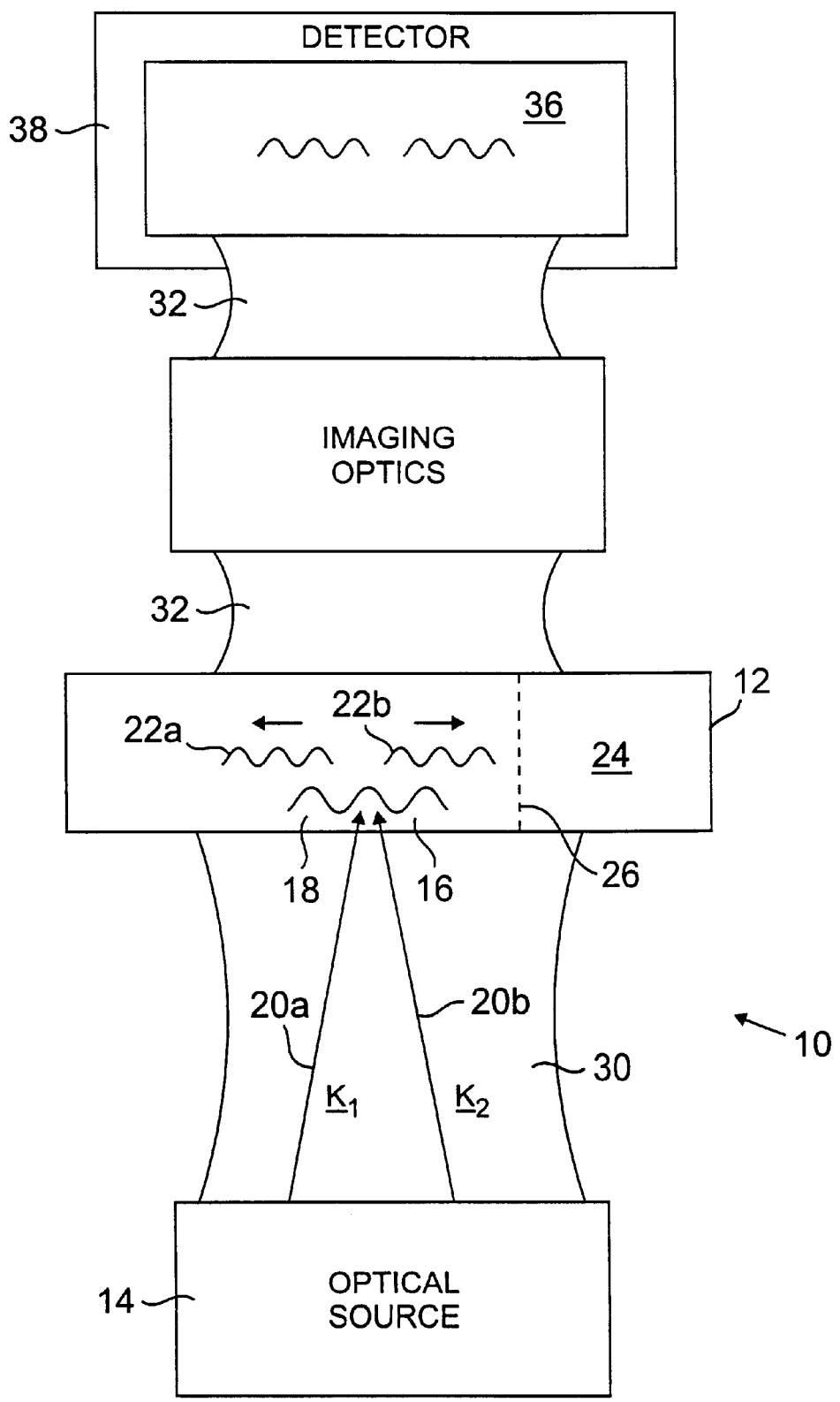
FIGS. 1a and 1b are schematics of a system for generating and imaging polariton waves in a sample.
Figure 1B:
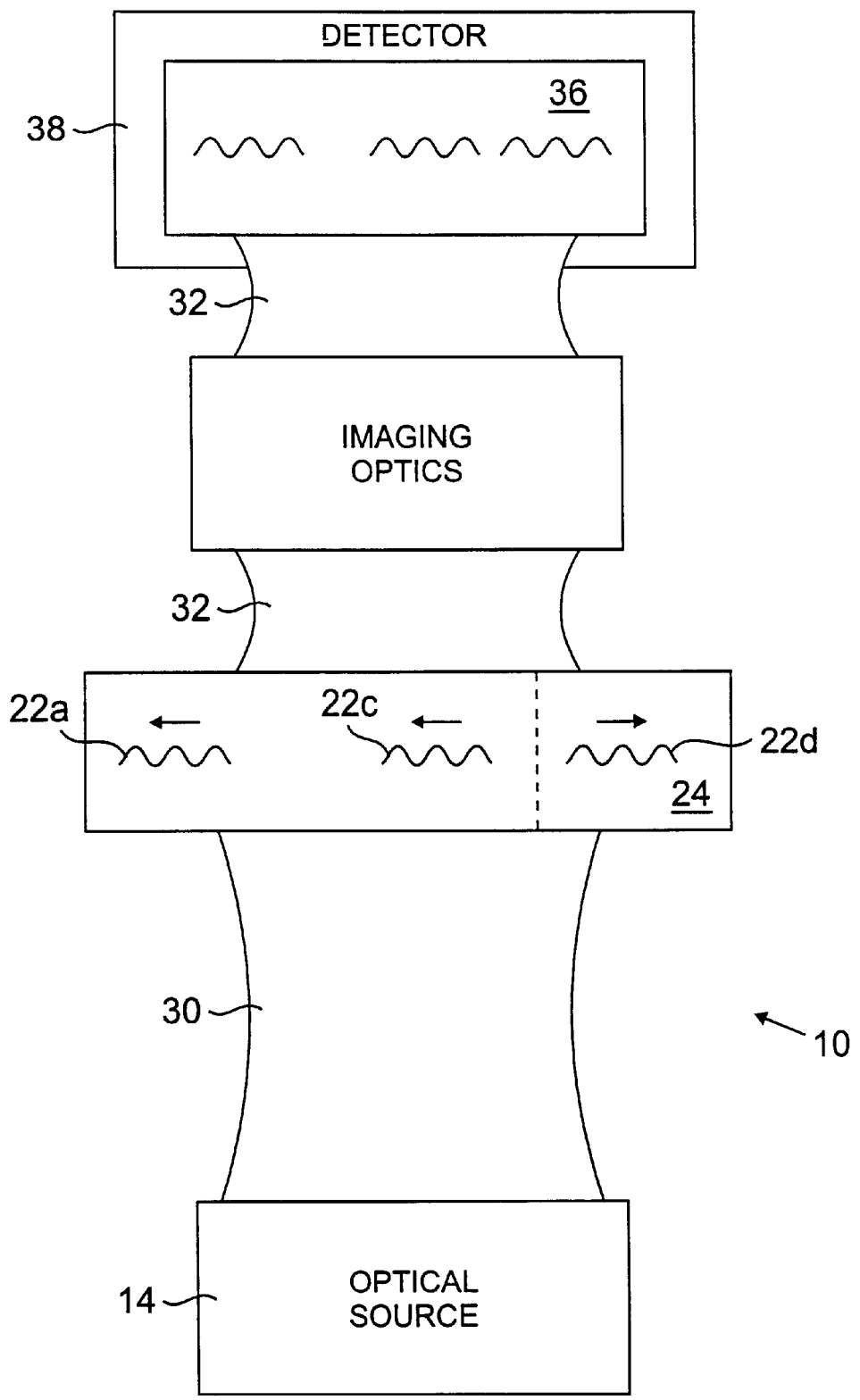

FIGS. 1a and 1b illustrate a schematic of a system 10 for spatial imaging of polariton waves in a material 12, which may be, e.g., a bulk, thin-film, or multilayer structure having at least one dielectric portion in which polariton waves may propagate. An optical source 14 generates optical excitation radiation, e.g., a pair of crossed, ultrashort laser pulses 20a and 20b that overlap at a first spatial region 18 in the material to form an optical interference pattern 16. Through nonlinear optical mechanisms such as impulsive stimulated Raman scattering (ISRS) or the electro-optic effect, optical interference pattern 16 excites counter-propagating polariton waves 22a and 22b, which propagate into other spatial regions of material 12. The polariton propagation may occur within or between bulk or thin-film layers of material 12, or along surfaces or interfaces of the material. This and other embodiments for the generation of polariton wave 16 will be described in greater detail below.

In the example shown in FIGS. 1a and 1b, a portion 24 of material 12 is doped, and therefore has physical properties different from the remainder of the material. Polariton wave 22b will scatter from the boundary 26 between the doped and undoped portions of material 12, producing a reflected polariton wave 22c and a transmitted polariton wave 22d, as shown in FIG. 1b. Since doped portion 24 has different physical properties, such as, e.g., a different refractive index, transmitted polariton wave 22d has a different phase velocity and fringe spacing from that of polariton waves 22a, 22b, and 22c.

After a time sufficient for the polariton waves to propagate, optical source 14 illuminates material 12 with optical probe radiation 30, e.g., an ultrashort probe pulse having an area sufficient to cover multiple spatial regions and overlap the propagating polariton waves. Since the polariton waves produce transient variations in the complex refractive index of the material as they propagate, portions of probe beam 30 that overlap the polariton waves undergo phase shifts related to the intensity of the propagating polariton waves to thereby produce a spatially-varying, phase-modulated probe beam 32. To properly resolve the polariton waves, the probe pulse should have a pulse duration shorter than a time period sufficient for the polariton waves to propagate a distance of interest. Alternatively, a long probe pulse or a continuous wave (cw) or quasi-cw probe beam could be used, with sufficient time resolution provided through optical gating or high speed detection electronics. Furthermore, if the probe pulse resolution is shorter than the inverse of the polariton phase velocity, individual fringes of the polariton waves may be resolved. The phase-modulated probe beam 32 is imaged using imaging optics 34 to produce an image 36 of the propagating polaritons, which is recorded by a spatially resolved detector 38, such as a charge couple device (CCD) camera. Particular embodiments for imaging optics 34 are described in further detail below.

Image 36 provides rapidly acquired and visually intuitive information about polariton propagation within material 12 and indicates inhomogeneities within material 12 such as boundary 24 and doped portion 26. Furthermore, source 14 can provide a series of time-delayed probe pulses to produce a corresponding time series of spatially-resolved images of polariton propagation, equivalent to a "movie", of polariton propagation within the sample.

Generation of Polariton Waves

Polariton waves occur when electromagnetic (EM) radiation couples to polar material modes, e.g., a molecular vibration, optic phonon, or exciton, in a material. In such materials, EM waves drive the polar material modes and the polar material modes radiate EM waves, thus the EM waves and the polar material modes couple to one another to form a polariton wave, i.e., a wave having an EM component and a material component corresponding to a displacement along the polar material mode. In many cases the polariton wave involves many polar material modes, which all couple to EM radiation.

Figure 2:
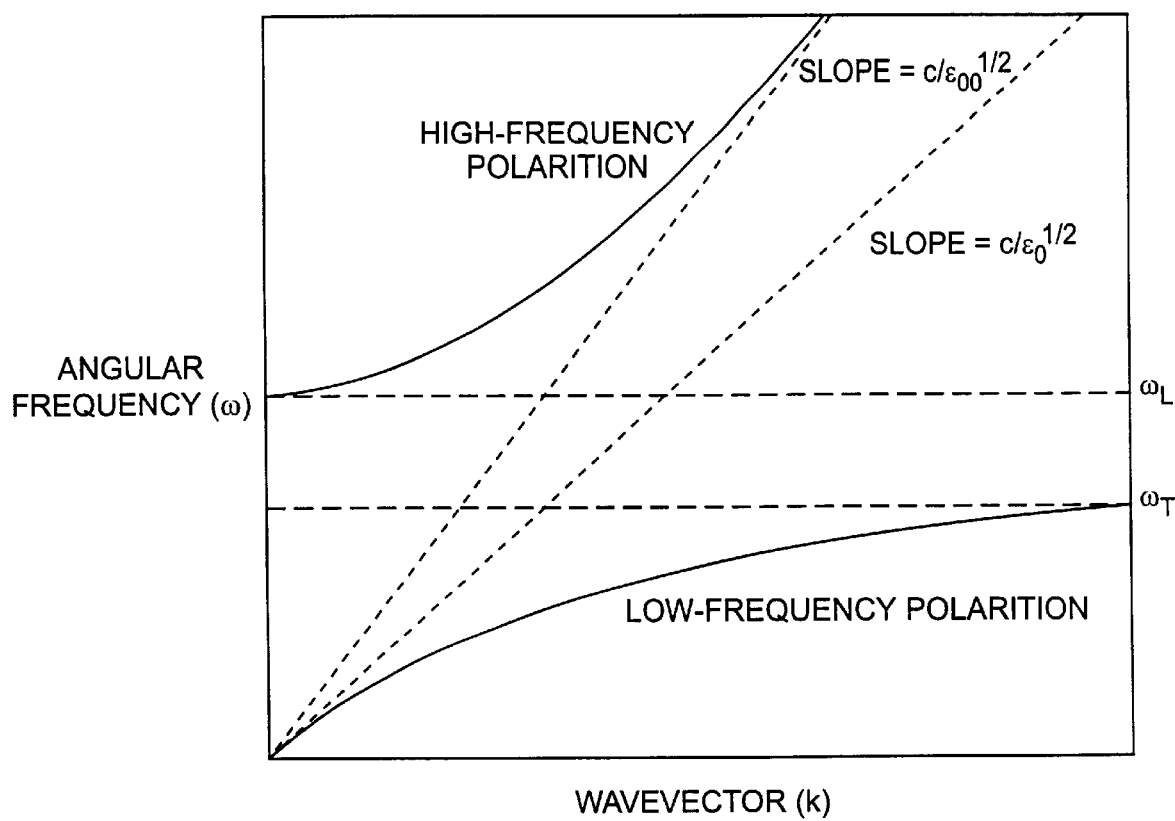
FIG. 2 is a dispersion curve for a polariton wave corresponding to a EM radiation coupling to a single polar, optic phonon in a bulk material.

Polariton waves are dispersive and they propagate through their host material. FIG. 2 shows the dispersion curve of a polariton wave in a bulk material in which EM radiation couples to a single polar optic phonon. Coupling between the EM radiation and the polar optic phonon is strongest in a relatively low wave vector regime where the EM frequency is comparable to the frequency of the optic phonon. As shown in FIG. 2, the coupling produces two polariton wave branches. The frequency of the lower branch approaches the transverse optic phonon frequency $\omega_L$ at large wave vector k, while the frequency of the higher branch approaches the longitudinal optic phonon frequency $\omega_L$ at small wave vector k. At large wave vectors k, the lower branch polariton predominantly involves only the material component and the upper branch predominantly involves only the EM component. For EM coupling to multiple polar, material modes, the polariton wave has multiple branches in the dispersion curve. Furthermore, in thin films, multilayer structures, and waveguides the polariton wave dispersion curves can be complicated, and are often determined numerically rather than analytically. In general, the polariton frequencies, typically of interest in the applications described herein are in the range of about 300 GHz to 10 THz.

Optical radiation in the visible and near infrared regions can generate the polariton waves through non-linear mechanisms such as impulsive stimulated Raman scattering (ISRS) and the electro-optic effect. Such mechanisms produce strong responses in materials including, e.g., lithium tantalate ($LiTaO_3$), lead titanate ($PbTiO_3$), potassium niobate ($Knbo_3$), barium titanate ($BaTiO_3$), potassium tantalate niobate ($KTa_{1-x}Nb_xO_3$), PZT ($KZr_xTi_{1-x}O_3$), PLZT ($K_{1-y}Li_yZr_xTi_{1-x}O_3$) crystals in the KDP and KTP families and organic crystals such as DAST.

In ISRS, an ultrashort (e.g., typically less than 200 fs) excitation pulse exerts a sudden ("impulse") force on those Raman-active modes whose vibrational periods are longer than the pulse duration. This sudden driving force produces time-dependent vibrational oscillations. For a general reference on ISRS see, for example, Y. Yan and K. A. Nelson (*J. Chem Phys.*, 87:6240, 1987. In non-centrosymmetric materials, the excited Raman-active vibrational modes can also be polar. In such cases, the time-dependent vibrational oscillations correspond to coherent oscillating dipoles, which generate and couple to electromagnetic radiation, thereby producing polariton waves. For a general reference on ISRS excitation of phonon-polaritons see, for example, T. P. Dougherty et al. (*J. Opt. Soc. Am. B.*, 9:2179, 1992).

To excite the polariton waves in material 12, source 14 provides an impulsive force, e.g., an optical intensity pattern, having a spatial profile that includes the wave vector corresponding to the frequency of the dispersive polariton waves of interest. As shown in FIG. 1*a*, the impulsive force can be produced by a pair of crossed excitation beams 20*a* and 20*b* having wave vectors $k_1$ and $k_2$, respectively. The beams can be, for example, 800 nm sub-100 fs pulses from a titanium sapphire laser. Beams 20*a* and 20*b* interfere with one another to form sinusoidal intensity interference pattern 16 (i.e., a grating) having a period equal to $2\pi/q$, where q equals the absolute value of $k_1-k_2$. Within each of the peaks of sinusoidal intensity profile 16, the optical radiation imparts an impulsive driving force on the Raman active modes within material 12. The overall driving force thus corresponds to a driving force having central wavevectors $\pm(k_1-k_2)$. Since the spotsizes of beams 20*a* and 20*b* are finite, a range of wavevectors is generated and polariton dispersion produces the two counter-propagating polariton wavepackets 22*a* and 22*b*, which have central wavevectors $\pm(k_1-k_2)$.

Single beam excitation, e.g., focused to a line or round spot, can also produce polariton waves through ISRS. For example, a tightly-focused, ultrashort excitation pulse can generate polariton waves through difference frequency mixing among the frequency components of the large bandwidth (i.e., ultrashort) pulse. However, in this case, the difference frequency components correspond to difference wavevectors existing within the tightly-focused pulse rather than from two crossed beams. As a result, exciting the crystal with a single pulse generates relatively low wavevector polariton waves, with the range of wavevectors inversely proportional to the spot size of the excitation pulse.

Another non-linear mechanism that can produce polariton waves is the electro-optic effect, which can occur in response to an ultrashort visible pulse similar to that used in the ISRS mechanism. In the electro-optic effect, a non-linear response in material 12 rectifies the ultrashort visible excitation pulse to produce a short burst of terahertz radiation that couples to polar material modes, thereby forming polariton waves. For the electro-optic effect, the optical excitation radiation can include single or multiple beams. As described previously, if a single tightly-focused excitation pulse is used, only relatively low wavevector polariton waves are generated, with a range inversely proportional to the spot size of the excitation pulse.

For both ISRS, the electro-optic effect, and other non-linear optical mechanisms, it is not necessary that the optical excitation radiation be tightly focused. In some embodiments, the optical excitation radiation can be, e.g., a large spot or an interference produced by crossing two beams with large spots. In such cases, polariton waves are generated throughout the excitation area and may propagate within that generation area for a substantial amount of time before exiting the area.

In addition to the single, crossed beam, and large spot spatial excitation profiles described above, the optical excitation radiation can have more complicated spatial profiles. In general, the polariton waves generated correspond to the wave vector content of the spatial intensity profile of the optical excitation radiation, subject to symmetry and pulse duration considerations. The optical excitation radiation can also have temporal profiles more complex than a single, ultrashort pulse, for example, it can include multiple pulses. What is important is that there is sufficient frequency bandwidth in the optical excitation radiation to excite by difference frequency mixing the polariton waves having wavevectors corresponding to the spatial profile of the optical excitation profile. In many cases, this implies that the optical excitation radiation have bandwidth sufficient to produce an optical pulse shorter than about 10 ps, i.e., a bandwidth greater than about 100 GHz, in some cases shorter than 50 fs, a bandwidth greater than about 20 THz. The central frequency for the optical radiation is typically in the ultraviolet, visible, or near-infrared, e.g., wavelengths in the range of about 300 nm to 2 microns. For references on generating shaped temporal and spatial excitation profiles that may be used to excite or image the polariton waves, see, e.g., U.S. Pat. Nos. 5,682,262 and 5,719,650, the contents of which are incorporated herein by reference.

In other embodiments, the polariton waves can be generated using frequency-domain, rather than time-domain excitation schemes. For example, rather than having difference-frequency mixing between components of an ultrashort pulse to excite a polariton wave, the difference frequency mixing between multiple, single frequency beams can excite the polariton wave through, e.g., stimulated Raman scattering (SRS) or other frequency-domain non-linear mixing mechanisms. For examples, two beams having frequencies $\omega_1$ and $\omega_2$, where $+/-(\omega_1-\omega_2)$ equals the frequency of the polariton wave, can be crossed with one another to excite the polariton waves.

In the non-linear optical generation of polariton waves described above, optical excitation radiation propagates through a thickness of material 12 and generates polariton waves propagating substantially perpendicular to the direction of the optical excitation radiation. This results from the non-linear mixing of wave vector and frequency components of the optical excitation radiation. However, because the optical excitation radiation generates polariton waves as it travels throughout the thickness of the material, there is also a small forward wave vector component to the overall polariton response.

The polariton waves can also be generated using methods different from non-linear optical methods. For example, low frequency EM radiation, e.g., 100 GHz to 20 THz, that propagates into material 12 directly excites the polar material modes that form the material component of the polariton waves, therefore this EM radiation propagates as a polariton wave within material 12. Similarly, a high-bandwidth electrical signal in a conductor adjacent a dielectric portion of material 12 can drive the polar, material modes in material 12, thereby producing the polariton waves.

Once generated, the polariton waves propagate according to the dispersion properties of their wavevector content and may then be mediated by inhomogeneities in material 12 that produce polariton wave scattering. Such inhomogeneities may include crystalline defects, domain wall boundaries, patterned features, and other features fabricated deliberately or otherwise present that may scatter polariton waves. In addition, since electrical signals are known to alter the dielectric tensor of non-centrosymmetric materials, and since polariton scattering can occur due to inhomogeneities in the dielectric tensor, transient or dc electrical signals can produce polariton scattering, which can be imaged. In particular, signals and inhomogeneities in structures that are in close proximity to dielectric regions of material 12 supporting the polariton waves can be detected. For example, polariton waves in a ferroelectric thin film that is on or in close proximity to a silicon substrate can detect signals in the substrate or in intervening layers between the film and the substrate.

Imaging the Polariton Waves

As shown in FIG. 1b, optical source 14 produces optical probe radiation 30 that images the polariton wave after a time interval t following their generation. Such a time interval between the excitation and probe radiation produced by source 14 can be introduced using, e.g., optical or electronic delay lines known in the art. Probe radiation 30 has a spot size large enough to illuminate the entire area of interest in material 12, i.e., the area over which polariton propagation is anticipated. Typically, the spot size of the probe radiation is in the range of about 500 microns to 2 cm, and in some cases of these cases it is in the range of about 1 mm to 5 mm. The wavelength of the optical probe radiation is typically in the ultraviolet, visible, or near-infrared regions, e.g., in the range of about 300 nm to 2 microns.

The polariton waves alter the refractive index n(r,t) of material 12 as they propagate through spatial position r of the material after time interval t. This variation in refractive index modifies the phase front of probe radiation 30 so that amplitude and phase of the polariton wave is mapped onto the probe radiation. To resolve the polariton propagation, the time duration of the probe radiation must be shorter than a time sufficient for the polariton wave to propagate a distance of interest. For example, if the group velocity of the polariton wave perpendicular to the direction of the probe radiation is one tenth the speed of light, a duration of one picosecond resolves distances on the order of 30 microns. Moreover, to resolve individual cycles of the polariton wave within the polariton wavepacket, the duration of the probe radiation must be shorter than the inverse of the polariton frequency. For example, if the polariton frequency was 2 THz, the duration should be shorter than 500 fs. In many cases, the duration of the probe radiation is in the range of about 30 to 300 fs, though for some applications durations on the order of picoseconds are sufficient.

In some cases, the resolution of the probe radiation is reduced by a velocity mismatch between the forward component of the polariton wave, i.e., the speed of the polariton wave in the direction of the probe radiation, and speed of light of the probe radiation in material 16. However, this mismatch is typically minimized when the polariton wave is both generated and imaged optically with excitation and probe radiation having similar wavelengths.

Upon being transmitted through material 16, the phase front of optical probe radiation will have undergone a spatially varying phase shift associated with variations in refractive index n(r,t) caused by the polariton wave. The total phase shift involves the integral of n(r,t) over the thickness of material 16. As shown in FIG. 1b, the phase-modulated probe radiation 32 is directed onto a spatially-resolved detector 38 using imaging optics 34. Imaging optics 34 may include spatial and frequency filters to prevent the excitation radiation, e.g., beams 20a and 20b, or other undesirable light, e.g., second harmonic light produced from the overlapping beams in material 12, from reaching the detector. Phase-modulated probe radiation 32 is converted into amplitude modulation by imaging optics 34 so that detector 38 can record image 34. This conversion can be accomplished in a number of ways.

Figure 3A:
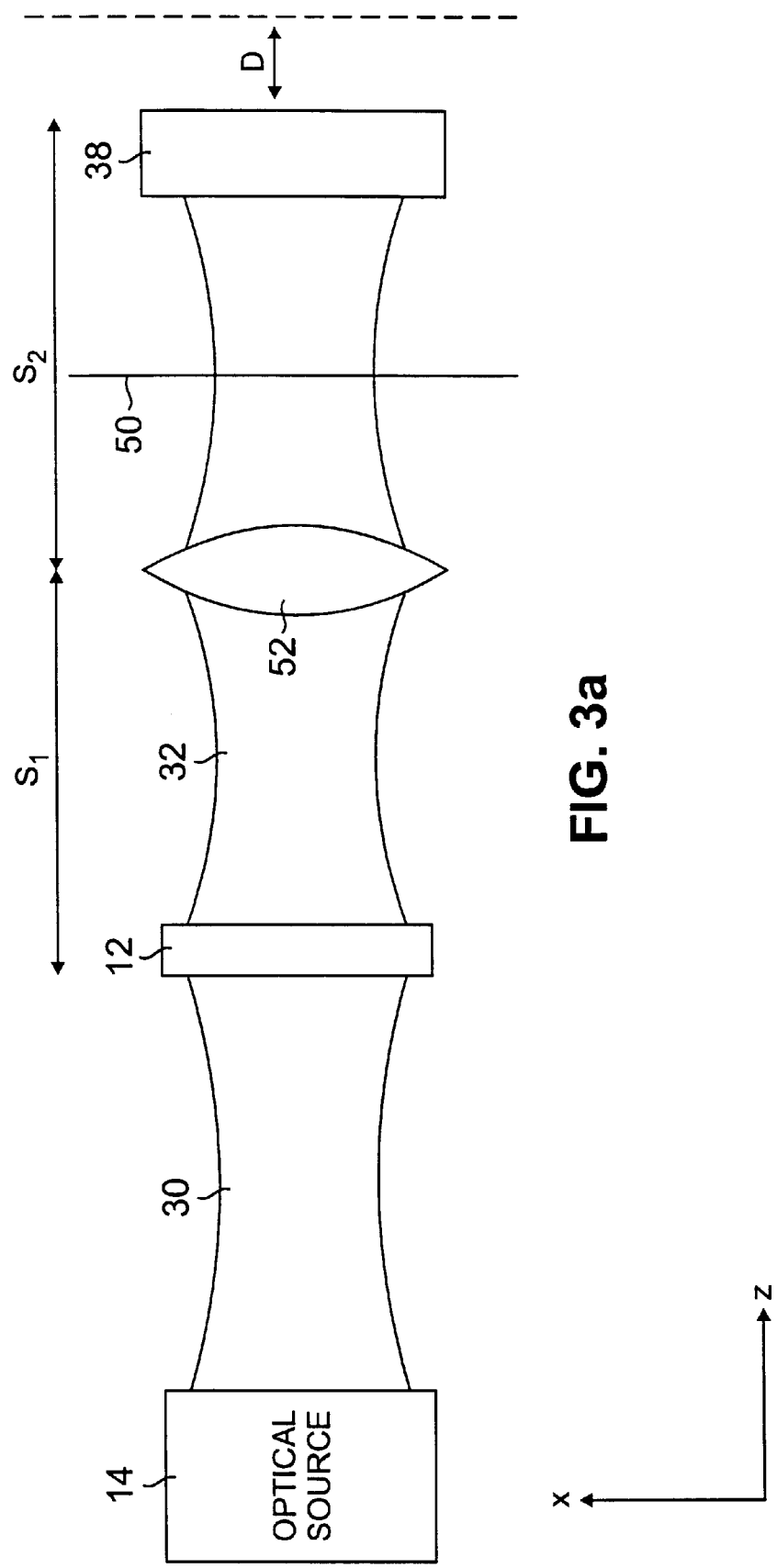
FIGS. 3a, 3b, and 3c are schematics of different embodiments for imaging polariton waves in a sample.

In one embodiment illustrated in FIG. 3a, imaging optics 34 can include a spatial filter 50 and a lens 52 having a focal length f. Filter 50 blocks the excitation radiation and prevents it from reaching detector 38, while allowing the probe radiation to pass. To make this possible, optical source 14 directs the probe radiation towards material 12 at an angle, e.g., a vertical angle, that is not parallel to the direction of the excitation radiation. Filter 50 is positioned in a plane where the probe and excitation radiation are most separated from one another, e.g., along the vertical y-axis direction.

Lens 52 is positioned a distance $s_1$ from material 12 and a distance $s_2$ from detector 38. If the distances $s_1$ and $s_2$ satisfy the well-known imaging formula for focusing images, $1/s_1 + 1/s_2 = 1/f$, then the phase modulation in the probe radiation in the plane of material 12 is entirely reconstructed in the plane of detector 38, and there is no amplitude modulation. However, if the distances do not satisfy the imaging formula, interference between different phase-modulated components of phase-modulated probe radiation 32 produces diffraction and amplitude modulation in the plane of detector 38. For example, to resolve the fringes of phase modulation imparted by the polariton wave in the material, detector 38 can be repositioned by a distance $D=(m+1/2)*d^2/\lambda$ from that distance which would satisfy the imaging formula, where m is an integer, d is the wavelength of the polariton wave, $\lambda$ is the wavelength of the optical probe radiation, and P in FIG. 3a is the position for detector 38 that satisfies the imaging formula. In such an arrangement, a sinusoidal phase grating with period d in the plane of material 12 is converted into a sinusoidal amplitude grating in the plane of detector 38, and thus image 36 recorded by detector 38 resolves the polariton propagation. In practice, the position of lens 52 or detector 38 is simply adjusted to optimally resolve the features of the polariton propagation. For a general reference on these type of self-imaging techniques, see, e.g., K. Patorski, "The self-imaging phenomenon and its applications," Vol. 27, pp. 1–108 in *Progress in Optics*, edited by E. Wolf (North-Holland, Amsterdam, 1989).

Other configurations are also possible. For example, the imaging formula can be satisfied and part of the phase-modulated probe radiation blocked, e.g., all of the negative orders of diffraction can be blocked, thus the recombination of diffracted components in the plane of the detector is incomplete, thereby producing amplitude modulation. For a reference, see, e.g., information about "phase-contrast" imaging and Schlieren imaging in M. Born and E. Wolf, *Principles of Optics*, (Pergamon Press, Oxford, 1980). Furthermore, rather than a single lens, i.e., lens 52, multiple lenses, e.g., a two-lens telescope, can be used.

Figure 3B:
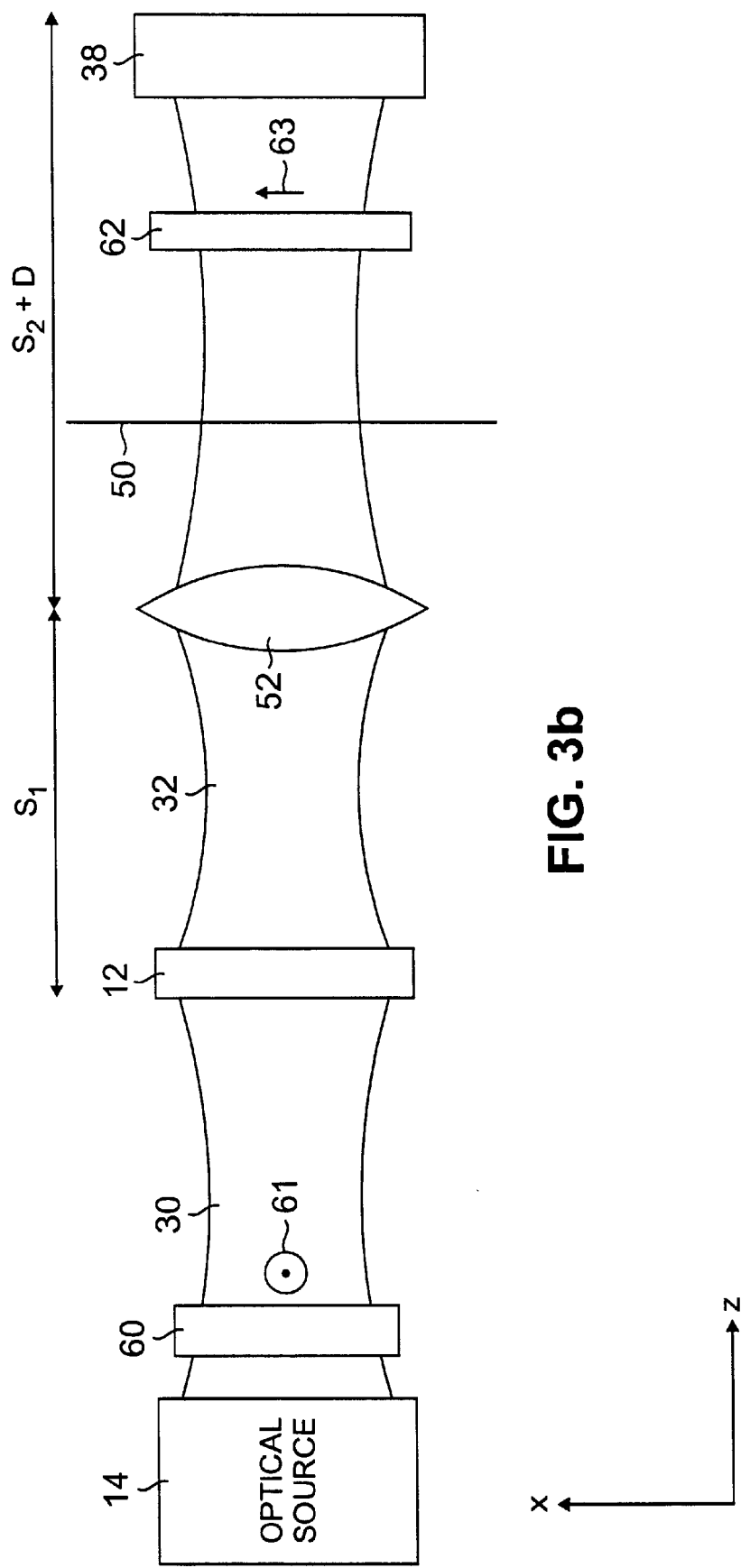

In many cases, the material component of the polariton wave actually imparts an anisotropic phase modulation in material 12 so that n(r,t) should be properly described as a tensor, with components that depend on the symmetry and orientation of the material. In such cases, the phase modulation imparted by the polariton waves onto phase-modulated radiation 32 can also be imaged using polarization rotation. For example, in another embodiment shown in FIG. 3b, a first polarizer 60 is positioned between optical source 14 and material 12 to produce probe radiation 30 that is linearly polarized along the y-axis, as indicated by symbol 61. The spatially-varying anisotropic phase-modulation imparted by polariton waves 22 in material 12 produces a spatially-varying elliptical polarization along the phase front of probe radiation 30. Lens 52 is positioned to image the phase-modulated probe radiation onto detector 38, e.g., by satisfying the imaging formula for $s_1$ and $s_2$, and a second polarizer 62 is oriented orthogonal to the first polarizer and blocks the initial linear polarization of the probe radiation, producing an amplitude-modulated probe radiation 64 at detector 38 corresponding to the phase modulation imparted by the polariton waves. Accordingly, the polarization of phase-modulated probe radiation 32 subsequent to second polarizer 62 is linearly polarized along the x-axis, as indicated by symbol 63. In this arrangement, the spatially-varying intensity of the probe radiation measured by the detector, known as a "homodyne" signal, is proportional to the spatially-varying intensity of the polariton wave.

In a modified arrangement, second polarizer 62 is oriented to pass a small amount of the initial linear polarization, i.e., the first and second polarizers are not quite orthogonal. The passed initial polarization mixes with the elliptical polarization produced by the polariton wave to produce a "heterodyne" signal. In this case, changes in the spatially-varying intensity measured by the detector are proportional to the spatially-varying amplitude of the polariton wave. In both homodyne and heterodyne arrangements, a phase compensator can be placed after sample 12 to compensate for static birefringence in the sample.

Figure 3C:
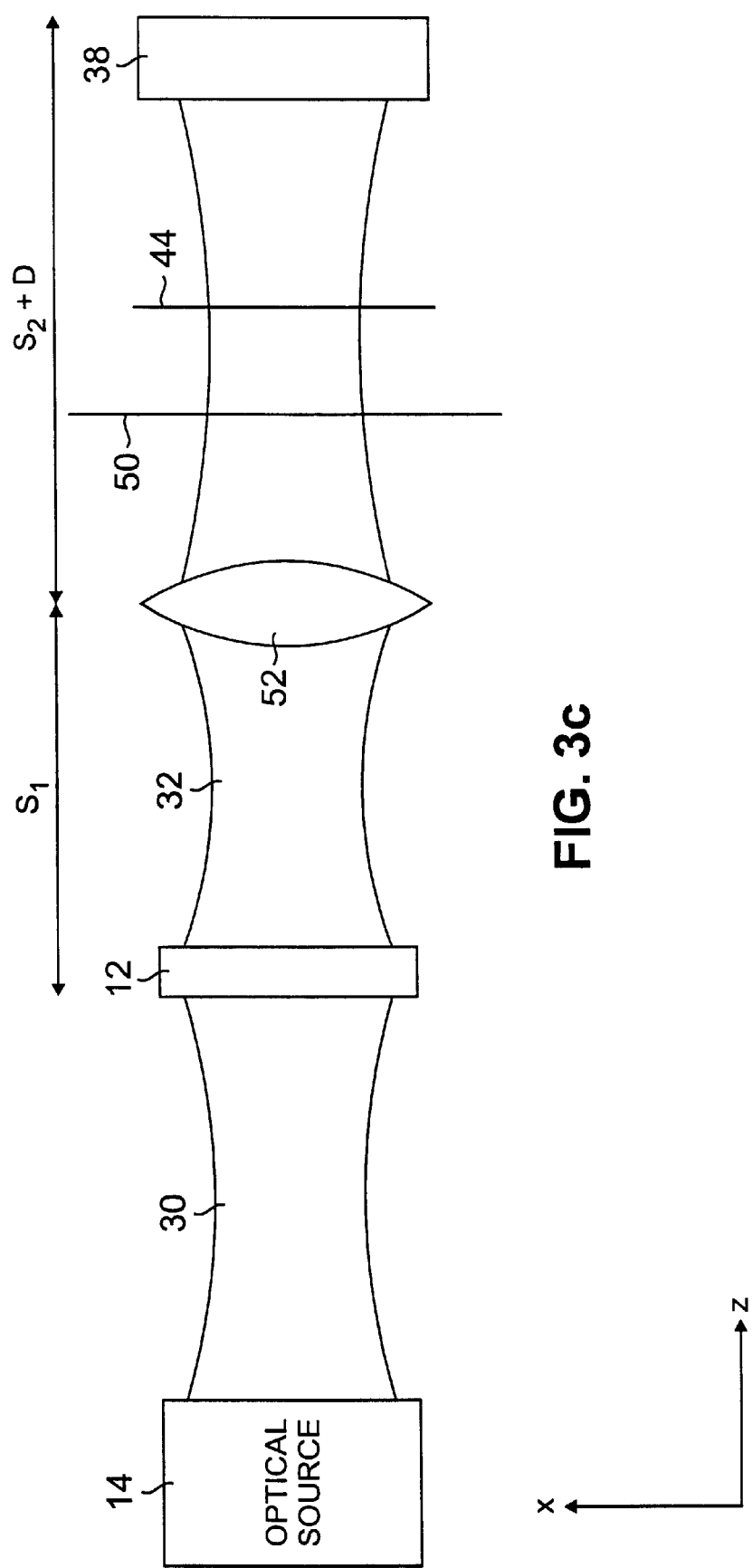

In another embodiment shown in FIG. 3c, the polariton waves can be imaged by spectral filtering of the optical probe radiation transmitted through material 12. In such embodiments, the polariton wave interacts with the optical probe radiation and downconverts ("red-shifts") or upconverts ("blue-shifts") the central wavelength of the optical probe radiation. The magnitude of the shift is related to the frequency of the polariton wave, and the direction of the shift, i.e., whether there is a red-shift or blue-shift, depends on the phase of the polariton wave when the probe radiation interacts with the polariton wave. To image the polariton propagation in this embodiment, a lens images the probe radiation in the plane of material 12 onto detector 38, e.g., according to the imaging formula, and a spectral filter 44 positioned before detector 38 transmits only red-shifted and/or blue-shifted probe radiation into detector 38.

In many embodiments, detector 38 may include image processing electronics, which carry out a background subtraction on the images recorded by the detector. For example, images can be recorded both before and after the polariton waves are generated, and the former image is subtracted from the latter image to produce image 36 of the polariton propagation. In this case, features in image 36 are causally dependent on the generation of the polariton waves.

By using a series of probe delay times, a series of polariton images can be produced, each corresponding to the polariton propagation a particular time interval following polariton generation. Such a series of images provide a "movie" of the polariton propagation.

Also, polariton waves can be imaged using reflected rather than transmitted probe radiation. For example, in reflective samples such as semiconductor thin films, surface and bulk polariton waves can vary the phase of probe radiation reflected from the surface of such samples through the complex index of refraction n(r,t). The phase-modulated reflected radiation can be converted into an image of the polariton propagation in a manner similar to phase-modulated transmitted radiation.

Furthermore, in some cases the polariton waves may impart amplitude modulation as well as phase modulation to the probe radiation through their affect on the imaginary part of the complex refractive index of material 12. Such modulation can be directly measured by detector 38.

Polaritons as Signal Carriers

In some applications, polariton waves are introduced into a waveguide or microcavity within a structure, such as a photonic crystal having one or more defects supporting the polariton waves. The polariton waves may carry signals to one or more objects connected to the waveguide. Such applications are described in U.S. Ser. No. 09/053,160 entitled "Methods and systems for introducing electromagnetic radiation into photonic crystals" by Keith A. Nelson et al., the contents of which are incorporated herein by reference. To diagnose such structures, insure that the polariton waves are propagating along the desired paths, and to characterize the signal paths, the polariton waves can be imaged in such structures using the techniques described herein.

EXAMPLES

The following non-limiting examples illustrate one of the methods for imaging polariton waves described herein.

Figure 4:
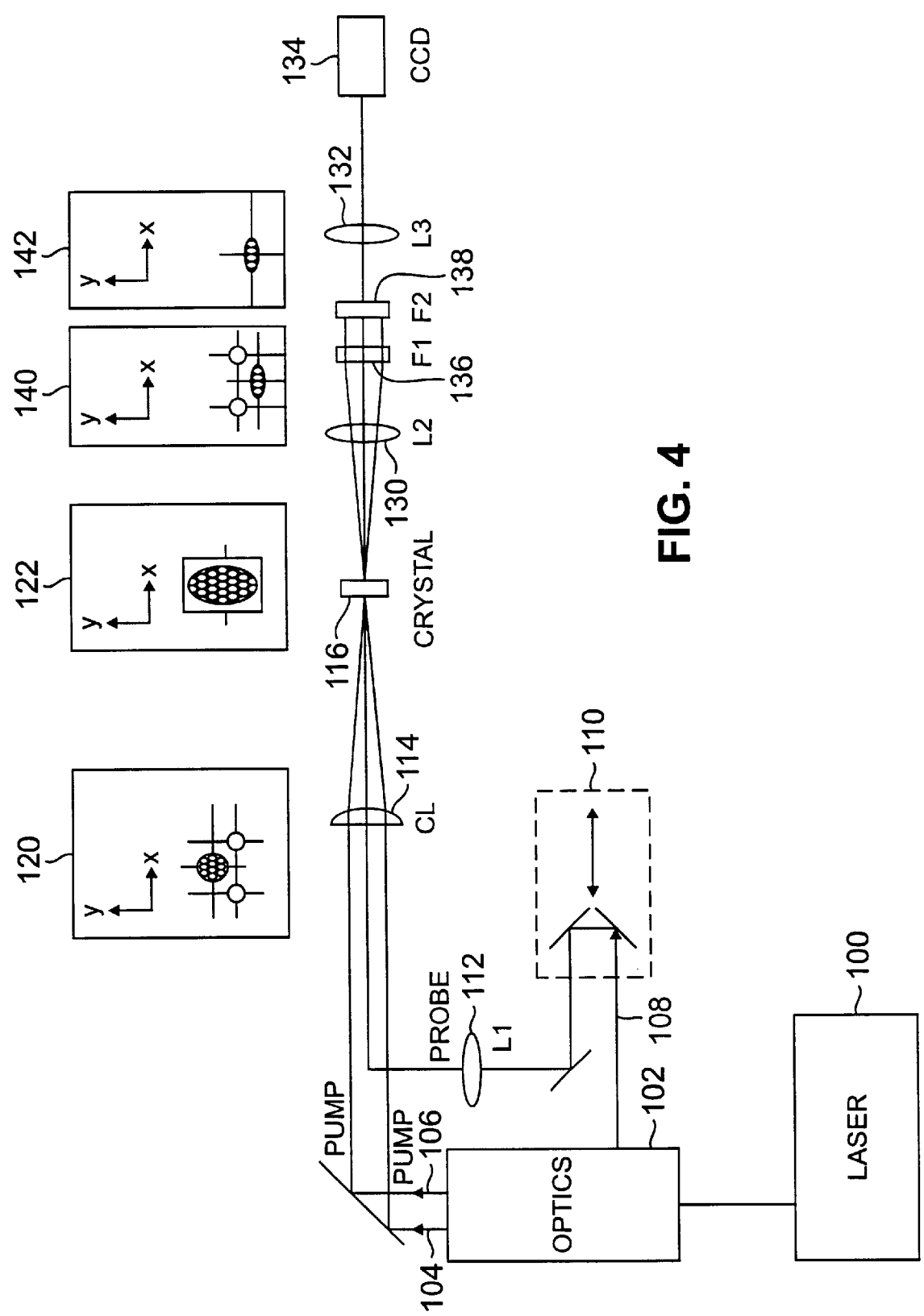
FIG. 4 is a schematic of an apparatus that was used to generate and image polariton waves.

As shown in FIG. 4, an amplified titanium sapphire laser system 100 produced 800 nm, 40 fs laser pulses having 0.1 mJ pulse energies at a repetition rate of 1 kHz. A series of beamsplitters and mirrors 102 split the laser pulses into two parallel pump beams 104 and 106 each carrying 20 µJ pulses and one probe beam 108 carrying 60 µJ probe pulses. Probe beam 108 passed through an optical delay line 110, which variably retards the probe pulses relative to the pump pulses, and then through a spherical lens 112. The pump and probe beams were then directed towards a cylindrical lens 114 having a focal length of 20 cm. Transverse profiles of the beams in the plane of the cylindrical lens 114 are shown in inset 120 with arrows marking x- and y-axes. In this and subsequent insets the pump beams are shaded and the probe beam is cross-hatched. At this point, the probe beam was vertically displaced from the parallel pump beams and propagating at a small vertical angle to the parallel pump beams.

Lens 114 focused the pump beams into overlapping lines on a 1-mm thick x-cut lithium tantalate crystal 116, the overlapping lines having widths of about 40–50 microns. The combination of lenses 112 and 114 produced a large spot size of about 2 mm for probe beam 108 on crystal 116, which overlapped and encompassed the pump lines. Transverse profiles of the beams in the plane of crystal 116 are shown in inset 122. The beamsplitters and mirrors 102 maintained equal path lengths for the two pump beams so that the pump pulses arrived simultaneously at crystal 116. Thus, the two pump lines interfered with one another to form a sinusoidal intensity grating along the x-axis, which generated polariton waves propagating in the +x and −x directions in the crystal. The wavevector q of the intensity grating was about 2100 cm$^{-1}$. Delay line 110 variably controlled the path length of probe beam 108 so that the probe pulse could arrive at the crystal both during, before, and after the pump pulses generated the polariton waves.

A two-lens telescope formed by lenses 130 and 132 imaged the probe beam in the plane of the crystal onto a CCD camera 134. A spectral filter 136 was positioned between lenses 130 and 132 to remove second harmonic light generated by the overlapping beams in the crystal. As shown in inset 140, the pump beams were vertically separated from the probe beam between lenses 130 and 132. A spatial filter 138 was positioned between lenses 130 and 132 to block the pump beams and prevent them from reaching CCD camera 134, as indicated in inset 142. Lenses 130 and 132 were spherical lenses having focal lengths of 10 cm and 16 cm, respectively. CCD camera 134 was positioned slightly out of focus by a distance of about a couple millimeters to resolve the features of the phase modulation imparted by the polariton waves on the probe beam.

FIGS. 5a–5f show images collected by the CCD camera for a number of different delay times between the pump and probe beams using the system in FIG. 4. The respective delay time is listed below each figure. The dimensions of the portion of the crystal displayed in the images are 0.895 mm by 2.05 mm. The image in FIG. 5a is taken when the probe pulse precedes the pump pulse, and therefore no polariton waves are visible. The image in FIG. 5b is taken when the probe and pump pulse are coincident and the strong signal near the center of the image is due to intense scattering and coherence effects of the coincident pulses. In the images shown in FIGS. 5c–5f, the polariton waves are visible, as indicated by the two sets of vertical lines moving away from the center of the images. These figures also indicate that the polariton waves are damped as they propagate. The erratic pattern near the center of each of the images may correspond to photorefractive damage caused by repeated exposure of the crystal to the pump beams or pump beam light not completely removed by spatial filter 138. Also, faint diagonal lines visible in the images are due to strong electrical noise in the laboratory environment.

Although only seven images are shown in FIGS. 5a–5g, two hundred and twenty images were recorded at 35 fs intervals. The digitized images have been sequentially combined with one another in a computer "movie" that illustrates the polariton motion in real time.

In a similar example, the CCD camera collected the images shown in FIGS. 6a–6g. In this case, a single pump beam was used to excite the polariton wave. The pump beam was focused by a spherical lens onto the crystal to a spot size of about 50 microns. FIGS. 6e–6g show counter-propagating hemispherical polariton waves emerging from the excitation region of the crystal. The response is anisotropic because the lithium tantalate crystal does not support polariton modes propagating along both transverse directions. These two example demonstrate optical imaging of polariton waves propagating within a sample.

Other aspects, advantages, and modifications are within the scope of the following claims.

What is claimed is:

1. A method for characterizing polariton propagation within a material, the method comprising:
    generating a polariton wave at a first spatial location in the material;
    waiting for a time interval sufficient to allow the polariton wave to propagate to additional spatial locations in the material; and
    optically imaging the polariton wave at the additional spatial locations.

2. The method of claim 1, wherein optically imaging comprises:
    directing optical radiation to the additional spatial locations; and
    generating a spatially-resolved image of portions of the optical radiation affected by the polariton.

3. The method of claim 1, further comprising:
    repeating the waiting and imaging steps for additional time intervals; and
    generating a spatially-resolved image of the polariton wave for each of the time intervals based on each of the imaging steps.

4. The method of claim 3, further comprising:
    identifying inhomogeneities in the material based on the images.

5. The method of claim 3, further comprising:
    detecting electrical signals within the material based on the images.

6. The method claim 1, wherein the polariton wave is generated by converting fast electrical signals adjacent the first spatial location into the polariton.

7. The method of claim 1, wherein the polariton wave is generated optically.

8. The method of claim 7, wherein the polariton wave is generated with an optical pulse having a duration shorter than 1 ps.

9. The method of claim 7, wherein the polariton wave is generating by crossing a pair of optical excitation beams on the material to form an optical excitation grating pattern at the first spatial location.

10. The method of claim 1, wherein the optical imaging is based on diffraction.

11. The method of claim 1, wherein the optical imaging is based on polarization rotation.

12. The method of claim 1, wherein the optical imaging is based on spectral filtering.

13. The method of claim 1, wherein the optical imaging is based on reflection.

14. The method of claim 2, wherein the optical radiation directed to the additional spatial locations is substantially larger than the first spatial location.

15. The method of claim 2, wherein the optical radiation directed to the additional spatial locations has a size greater than or equal to about 1 mm.

16. The method of claim 2, wherein the optical radiation directed to the additional spatial locations has a size that overlaps the first spatial location.

17. The method of claim 1, wherein the polariton wave has an electromagnetic frequency within the range of about 300 GHz to 20 THz.

18. The method of claim 1, wherein the material is a semiconductor or a ferroelectric.

19. A method for characterizing a polariton wave propagating within a waveguide, the method comprising:
    introducing the polariton wave into a first location of the waveguide;
    waiting for a time interval sufficient to allow the polariton wave to propagate to additional locations within the waveguide; and
    optically imaging the polariton wave at the additional spatial locations.

20. The method of claim 19, further comprising:
    repeating the waiting and imaging steps for additional time intervals; and generating a spatially-resolved image of the polariton wave for each of the time intervals based on each of the imaging steps.

21. The method of claim 18, wherein the waveguide is formed within a photonic crystal.

22. A method for characterizing a polariton wave within a material, the method comprising:

generating the polariton wave; and imaging the polariton wave with optical radiation to produce a spatially-resolved image of portions of the optical radiation affected by the polariton wave.

23. The method of claim 22, wherein the optical radiation is has a central wavelength in the range of about 300 nm to 2.5 microns.

* * * * *